(12) United States Patent
Choi et al.

(10) Patent No.: US 9,690,276 B2
(45) Date of Patent: Jun. 27, 2017

(54) CONTROLLER FOR SCENT DIFFUSING DEVICE AND A SERVER FOR SUPPORTING THE CONTROLLER

(71) Applicant: ELECTRONICS AND TELECOMMUNICATIONS RESEARCH INSTITUTE, Daejeon (KR)

(72) Inventors: Ji Hoon Choi, Daejeon (KR); Chung Hyun Ahn, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 68 days.

(21) Appl. No.: 15/016,557

(22) Filed: Feb. 5, 2016

(65) Prior Publication Data

US 2016/0231720 A1    Aug. 11, 2016

(30) Foreign Application Priority Data

Feb. 6, 2015    (KR) ........................ 10-2015-0018748

(51) Int. Cl.
*G05B 19/04*    (2006.01)
(52) U.S. Cl.
CPC .. *G05B 19/041* (2013.01); *G05B 2219/24151* (2013.01)
(58) Field of Classification Search
CPC ....................................................... A61L 19/12
USPC .......................................................... 239/34
See application file for complete search history.

(56) References Cited

U.S. PATENT DOCUMENTS

| | | | | |
|---|---|---|---|---|
| 5,949,522 A * | 9/1999 | Manne | ..................... | A61L 9/122 261/104 |
| 6,354,954 B1 * | 3/2002 | Sumner | .................. | A63G 31/16 472/45 |
| 6,556,272 B1 * | 4/2003 | Du | .......................... | A61L 9/035 352/85 |
| 7,734,436 B2 * | 6/2010 | Labreche | ............. | G06K 9/6253 702/81 |

(Continued)

FOREIGN PATENT DOCUMENTS

| | | |
|---|---|---|
| JP | 2005-326907 | 11/2005 |
| JP | 2011-155532 | 8/2011 |
| KR | 10-2011-0105625 | 9/2011 |

OTHER PUBLICATIONS oPhone DUO_Indiegogo, [https://www.indiegogo.com/projects/ophoneduo#/1].

*Primary Examiner* — Gene Crawford
*Assistant Examiner* — Stephen Akridge
(74) *Attorney, Agent, or Firm* — Kile Park Reed & Houtteman PLLC

(57) ABSTRACT

Disclosed are a customized scent diffusing device and a customized scent diffusing method for effectively transferring sensibility which can be felt from contents to a user by diffusing a most appropriate scent by synchronization with digital contents. According to various exemplary embodiments of the present invention, although odor effect information in 4D contents does not correspond to a spice cartridge configuration in a scent diffusing device, an appropriate odor can be provided through combining or mixing spice cartridges in the scent diffusing device.

9 Claims, 14 Drawing Sheets

(56) References Cited

U.S. PATENT DOCUMENTS

| | | | | |
|---|---|---|---|---|
| 2002/0066798 A1* | 6/2002 | Laudamiel-Pellet | A01M 1/2033 | 239/34 |
| 2003/0168524 A1* | 9/2003 | Hess | A61L 2/18 | 239/306 |
| 2003/0206834 A1* | 11/2003 | Chiao | A61L 9/014 | 422/124 |
| 2005/0278224 A1* | 12/2005 | Bannai | A61L 9/035 | 705/22 |
| 2007/0258849 A1* | 11/2007 | Kent | A61L 9/035 | 422/5 |
| 2011/0226864 A1* | 9/2011 | Kim | A61L 9/14 | 239/6 |
| 2013/0081541 A1* | 4/2013 | Hasenoehrl | A61L 9/035 | 96/222 |
| 2014/0113715 A1* | 4/2014 | Joo | A63F 13/02 | 463/30 |
| 2014/0115649 A1* | 4/2014 | Kim | H04N 21/234 | 725/116 |
| 2015/0297776 A1* | 10/2015 | Conroy | B05B 7/2416 | 239/11 |

* cited by examiner

FIG. 3

```
<DescriptionMetadata>
<ClassificationSchemeAlias alias="SCENT" href="urn:mpeg:mpeg-v:01-SI-ScentCS-NS"/>
</DescriptionMetadata>
<Effect xsi:vype="sev:ScentType" intensity-value="0.1" intensity-range="0.0 10.0" duration="10" scent=":SCENT:lilac" si:pts="0"/>
```

FIG. 4

| | DESCRIPTION |
|---|---|
| Scent_Information { | |
| scent_count | NUMBER OF SCENTS |
| for(scent_count) { | |
| scent_name | SCENT NAME |
| } | |
| cartridge_count | NUMBER OF SCENT CARTRIDGES OF SCENT DIFFUSING DEVICE |
| for(cartridge_count) { | |
| model_number | MODEL NUMBER OF CARTRIDGE |
| cartridge_name | NAME OF SCENT CARTRIDGE |
| vendor_name | VENDOR NAME |
| } | |
| } | |

FIG. 5

| Mapping_Table { | |
|---|---|
| scent_count | NUMBER OF ALTERNATE SCENTS |
| for(scent_count) { | |
| scent_name | NAME OF ALTERNATE SCENT |
| cartridge_name | NAME OF SPICE CARTRIDGE |
| operation_time | SCENT DIFFUSING TIME |
| scent_intensity | SCENT DIFFUSING CONCENTRATION |
| blower_speed | SCENT DIFFUSING SPEED |
| } | |
| } | |

FIG. 6

| STX (0x02) | Device ID | Command Type | Scent Count | Scent ID (n) | Operation Time(n) | Scent Intensity(n) | Blower Speed(n) | Tracking Flag | Swing Flag | ETX (0x03) |
|---|---|---|---|---|---|---|---|---|---|---|

N SCENTS (Scent ID(n) through Blower Speed(n))

FIG. 11

| NAME OF COMPOSITE SCENT | NO. OF COMPOSITE SCENT | NO. OF REFERENCE SCENT AND CONCENTRATION LEVEL | | | | | | | | MEMBERSHIP GRADE WITH CENTER OF REFERENCE SCENT(%) | | | |
|---|---|---|---|---|---|---|---|---|---|---|---|---|---|
| 0000 | 00 | 0000 1000 | 0001 1000 | 0010 1000 | 0011 1000 | | | | | 30 | 18 | 25 | 27 |
| 0000 | 01 | 0000 1001 | 0001 0111 | 0010 0110 | 0011 1010 | | | | | 36 | 15 | 24 | 27 |
| 0000 | 10 | 0000 0111 | 0001 1010 | 0010 0111 | 0011 0111 | | | | | 27 | 22 | 25 | 26 |
| 0000 | 11 | 0000 1010 | 0001 0110 | 0010 1010 | 0011 0110 | | | | | 38 | 14 | 23 | 25 |
| 0001 | 00 | – | – | – | – | | | | | – | – | – | – |
| 0001 | 01 | – | – | – | – | | | | | – | – | – | – |
| 0001 | 10 | – | – | – | – | | | | | – | – | – | – |
| 0001 | 11 | | | | | | | | | | | | |

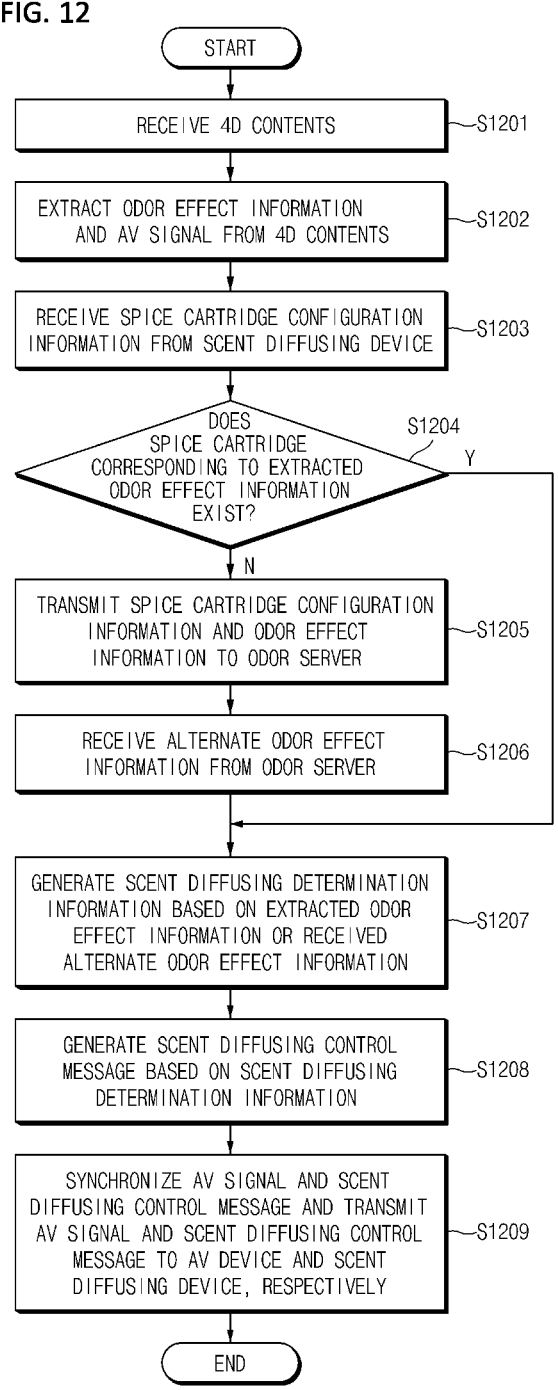

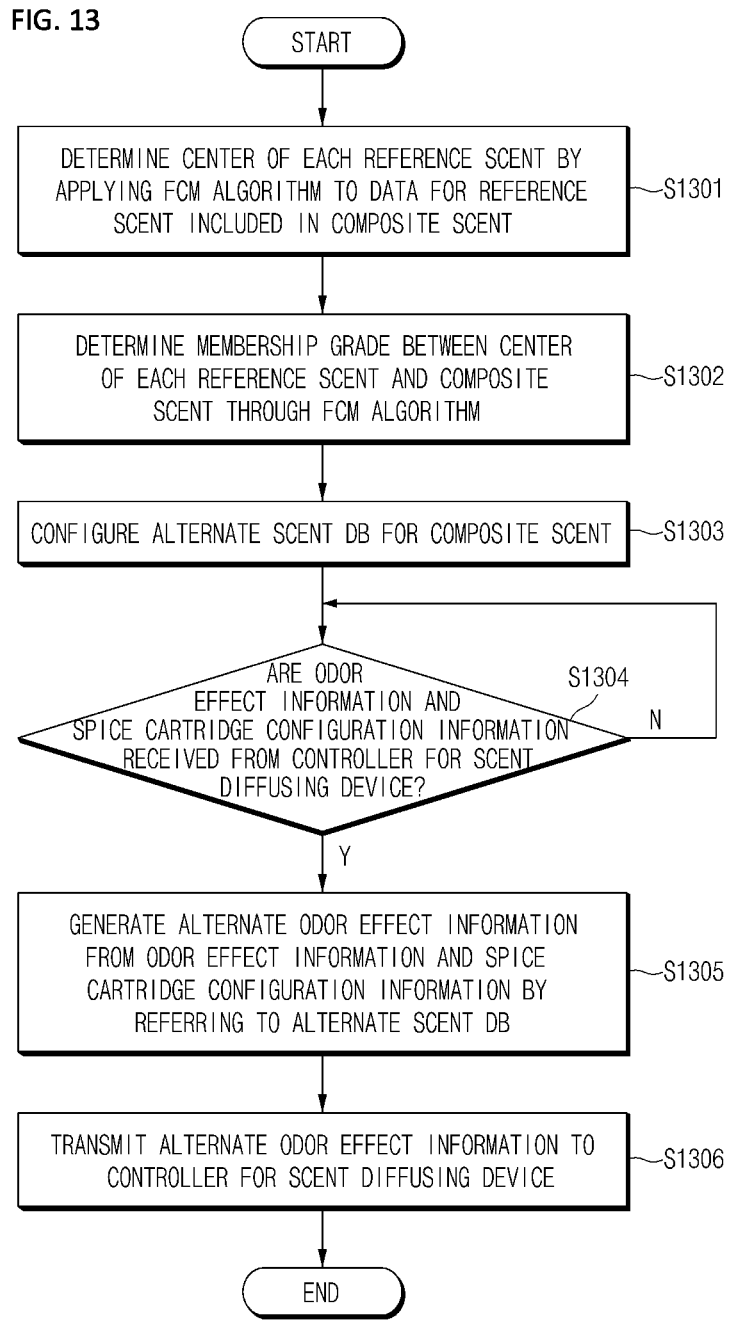

CONTROLLER FOR SCENT DIFFUSING DEVICE AND A SERVER FOR SUPPORTING THE CONTROLLER

CROSS-REFERENCE TO RELATED APPLICATIONS

This application claims priority to and the benefit of Korean Patent Application No. 10-2015-0018748 filed in the Korean Intellectual Property Office on Feb. 6, 2015, the entire contents of which are incorporated herein by reference.

TECHNICAL FIELD

The present invention relates to a controller for a scent diffusing device for effectively transferring sensibility which can be felt from the contents to a user by diffusing a most appropriate scent by synchronization with digital contents and a server for supporting the controller.

BACKGROUND ART

Contents in which a 3D effect of contents can be visually felt are generally referred to as "3D contents" and apart therefrom, contents which can stimulate five senses of a user including a visual sense, a hearing sense, an olfactory sense, and the like are referred to as "4D contents".

In recent years, 4D contents have been primarily played at a theater or a special cinema, but a consumption area of the 4D contents has been gradually extended indoors. That is, in addition to a study for providing predetermined 4D contents to spectators for a special cinema, a study for providing various 4D contents transmitted from a broadcasting station to users in a household even in a general household has been in active progress.

To this end, the study makes an effort to implement an audio video (AV) device capable of providing 4D contents and a 4D effect reproducing device (in particular, scent diffusing device). In recent years, Moving Picture Experts Group (MPEG) which is an international standardization organization for multimedia contents has defined interface standards for communication between a virtual world and the virtual world and between the virtual world and a real world through an MPEG-V project (ISO/IEC 23005).

SUMMARY OF THE INVENTION

AV contents which can be transmitted to a general household can be very diversely provided with video and sound processing technologies in the related art, while a type of scent (alternatively, odor) which can be provided by a scent diffusing device in the related art is limited to a type of scent cartridge mounted on the device. Due to such a limit, it was difficult for scent diffusing devices in the related art to provide an optimal scent according to a scene or an environment of the AV contents. In particular, when the scent diffusing device does not include a scent cartridge suitable for a specific scene of the AV contents, there is a limit that a wrong scent is provided to a user or no scent can be provided.

The present invention has been made in an effort to provide a controller for a scent diffusing device which can provide an appropriate alternate odor to a user even though the controller includes only a limited spice cartridge.

Other technical objects and solving means of the present invention may be appreciated by the following description and will be more apparent by exemplary embodiments of the present invention. Further, the technical objects and the solving means of the present invention may be realized by means described in the claims and a combination thereof.

An exemplary embodiment of the present invention provides a controller for a scent diffusing device for controlling a scent diffusing device including a plurality of spice cartridges, including: an analysis module determining an odor to be generated by the scent diffusing device based on odor effect information received from the outside and configuration information of the plurality of spice cartridges; and a control module transmitting a scent diffusing control message corresponding to the determined odor to the scent diffusing device.

According to various exemplary embodiments of the present invention, an appropriate alternate odor can be provided to a user even though only a limited spice cartridge is provided. In particular, when a 4D content originator produces 4D contents only with an odor (that is, a reference scent) which can be most basic or representative, the user can receive an appropriate odor through a controller for a scent diffusing device according to various exemplary embodiments of the present invention. As a result, the user can sufficiently receive an emotion which is felt from contents.

The exemplary embodiments of the present invention are illustrative only, and various modifications, changes, substitutions, and additions may be made without departing from the technical spirit and scope of the appended claims by those skilled in the art, and it will be appreciated that the modifications and changes are included in the appended claims.

BRIEF DESCRIPTION OF THE DRAWINGS

FIG. 3 illustrates one example of odor effect information according to an exemplary embodiment of the present invention.

FIG. 4 illustrates a data structure of spice cartridge configuration information according to an exemplary embodiment of the present invention.

FIG. 5 illustrates a data structure of alternate odor effect information according to an exemplary embodiment of the present invention.

FIG. 6 illustrates a scent diffusing control message according to an exemplary embodiment of the present invention.

FIG. 11 illustrates one example of a data structure of an alternate odor DB according to an exemplary embodiment of the present invention.

FIG. 12 is a flowchart illustrating an operation of a controller 10 for a scent diffusing device according to an exemplary embodiment of the present invention.

FIG. 13 is a flowchart illustrating an operation of an odor server according to an exemplary embodiment of the present invention.

Figure 1:
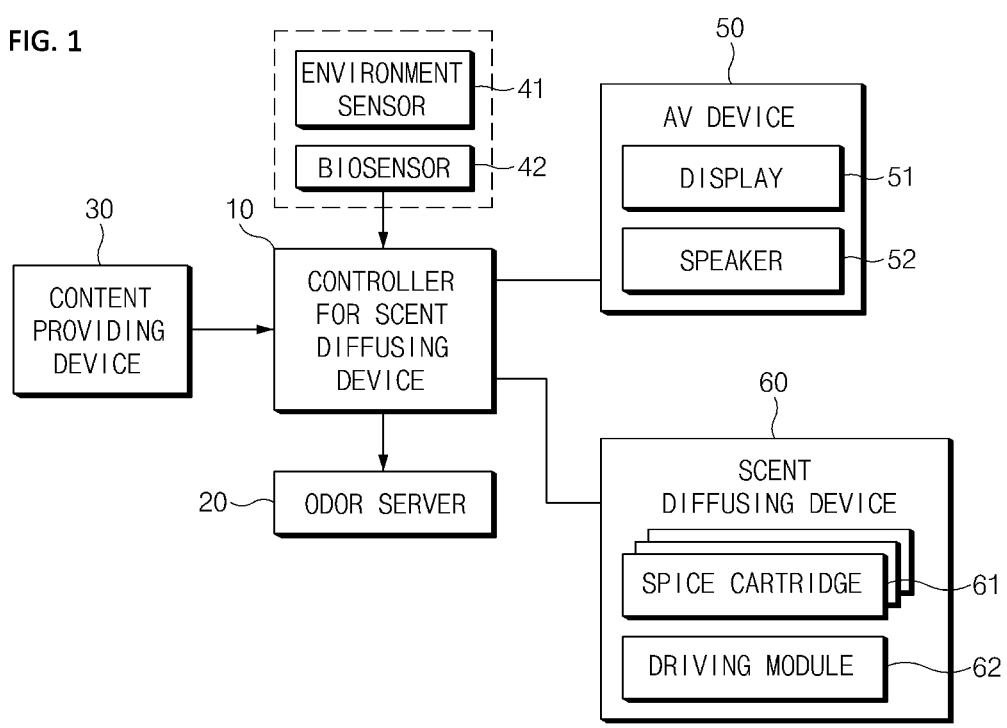
FIG. 1 illustrates a scent diffusing system to which a controller for a scent diffusing device can be applied according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present invention may have various modifications and various embodiments and specific embodiments will be illustrated in the drawings and described in detail in the detailed description. However, this does not limit the present invention to specific exemplary embodiments, and it should be understood that the present invention covers all the modifications, equivalents and replacements included within the idea and technical scope of the present invention. Further, in the following description, a detailed explanation of known related technologies may be omitted to avoid unnecessarily obscuring the subject matter of the present invention.

Terms used in the present application are used only to describe specific exemplary embodiments, and are not intended to limit the present invention. Singular expressions used herein include plural expressions unless they have definitely opposite meanings in the context. In the present application, it should be understood that the term "include" or "have" indicates that a feature, a number, a component, a part or a combination thereof described in the specification is present, but does not exclude a possibility of presence or addition of one or more other features, numbers, components, parts or combinations thereof, in advance.

Hereinafter, exemplary embodiments of the present invention will be described in detail with reference to the accompanying drawings.

FIG. 1 illustrates a scent diffusing system to which a controller for a scent diffusing device can be applied according to an exemplary embodiment of the present invention.

Referring to FIG. 1, the scent diffusing system to which the controller for a scent diffusing device can be applied according to the exemplary embodiment of the present invention may include a controller 10 for a scent diffusing device, an odor server (hereinafter, just also referred to as a server) 20, a content providing device 30, an environment sensor 41, a biosensor 42, an AV device 50, and a scent diffusing device 60.

The scent diffusing controller 10 may determine an odor to be diffused by the scent diffusing device 60 based on various information received from the content providing device 30, the environment sensor 41, and the biosensor 42. The odor provided from the scent diffusing device 60 may be diffused in synchronization with audiovisual contents output from the AV device 50.

The scent diffusing controller 10 may determine that an odor corresponding to 4D contents received from the content providing device 30 may not be provided to respective single spice cartridges 61 provided in the scent diffusing device 60. The scent diffusing controller 10 may transmit odor effect information and spice cartridge configuration information (of the 4D contents provided by the content providing device 30) to the odor server 20 and receive alternate odor effect information to correspond to the transmitted odor effect information and spice cartridge configuration information. By this configuration, the scent diffusing controller 10 may control the scent diffusing device 60 to provide an alternate odor (e.g., a composite scent) to a user through a combination of a plurality of spice cartridges 61.

The odor server 20 may provide alternate odor effect information to the scent diffusing controller 10 based on the odor effect information and spice cartridge configuration information (of the 4D contents provided by the content providing device 30). The alternate odor effect information may be information on the composite scent which may be generated by combining (mixing) the plurality of spice cartridges 61.

The content providing device 30 may transmit the 4D contents to the scent diffusing controller 10. The 4D contents may mean contents which may stimulate five senses of the user, which include a visual sense, a hearing sense, an olfactory sense, and the like. The 4D contents according to the exemplary embodiment of the present invention may include an AV signal and the odor effect information. According to the exemplary embodiment, the odor effect information may be included in broadcasting organization information of the 4D contents.

The content providing device 30 may be generally provided in a digital TV broadcasting station and an Internet content providing server. Further, according to the exemplary embodiment, the content providing device 30 may be implemented in the form of a storage device (memory) storing the 4D contents.

The environment sensor 41 may detect environment information, that is, a temperature, a humidity, a direction/strength of wind, a position/distance of the scent diffusing device, and the like. The environment sensor 41 may provide the environment information to the scent diffusing controller 10 periodically or in real time.

The biosensor 42 may include, for example, a heartbeat sensor or a body temperature sensor. Emotional states (pleasure, sadness, anger, depression, and the like) of the user may be derived from bio information measured from the biosensor 42. The bio sensor 42 may periodically provide the bio information to the scent diffusing controller 10. According to the exemplary embodiment, the emotional states of the user are input from the user to be used for controlling the scent diffusing device 60.

The AV device 50 may include a display 51 and a speaker 52. The AV device 50 may provide the audiovisual contents to the user based on the AV signal received from the scent diffusing controller.

The scent diffusing device 60 may include one or more replaceable spice cartridges 61 and driving modules 62. The scent diffusing device 60 may receive a scent diffusing control message from the scent diffusing controller 10. The scent diffusing device 60 may eject spices included in the spice cartridge 61 based on a scent diffusing time, a scent diffusing concentration, a scent diffusing speed, scent diffusing direction information, and the like according to the scent diffusing control message. The spice may be ejected (that is, diffused) in synchronization with the AV contents from the AV device 50. As a result, the user may receive the 4D contents through the visual sense, the hearing sense, and the olfactory sense.

Figure 2:
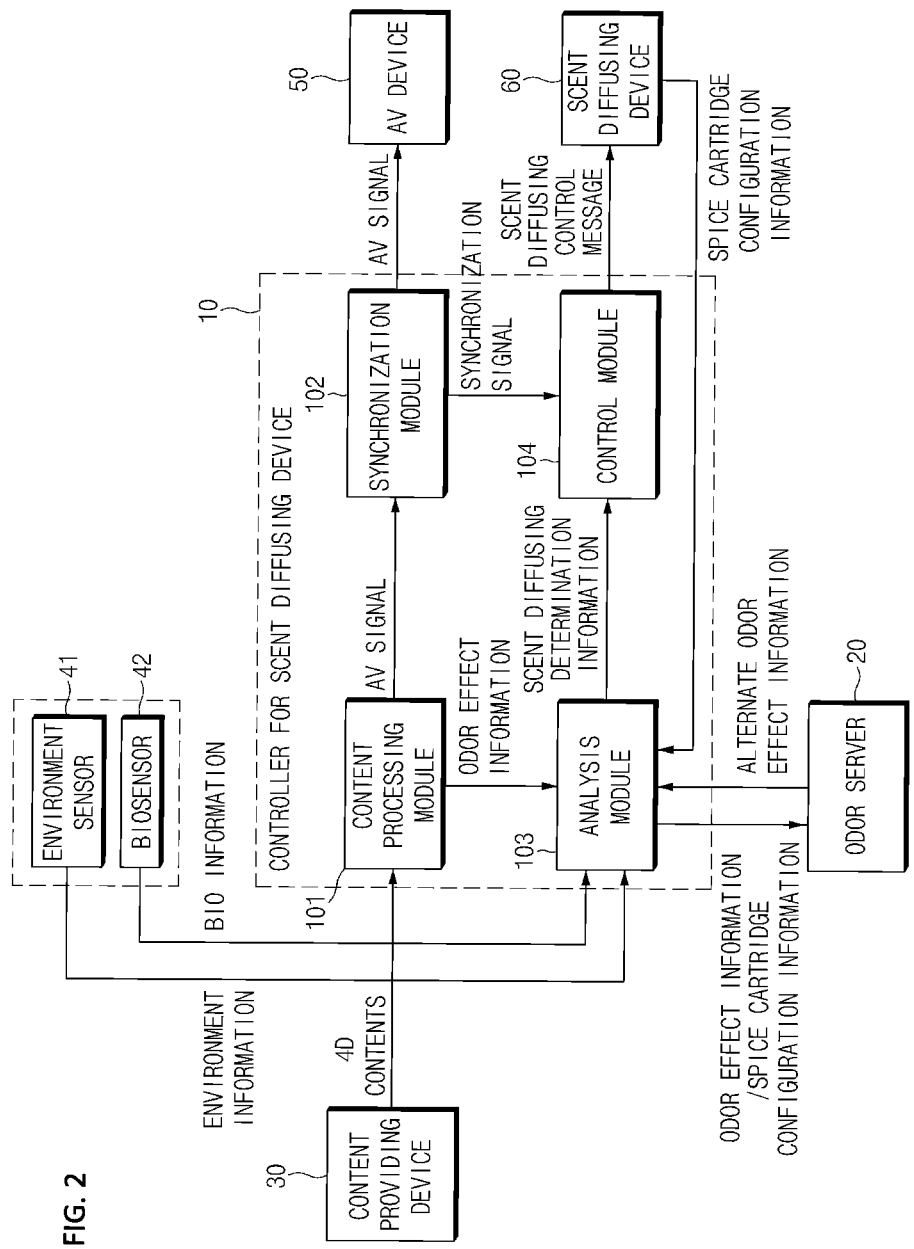
FIG. 2 is a block diagram of the controller for the scent diffusing device according to an exemplary embodiment of the present invention.

FIG. 2 is a block diagram of the controller for the scent diffusing device according to an exemplary embodiment of the present invention.

Referring to FIG. 2, the scent diffusing controller 10 according to the exemplary embodiment of the present invention may include a content processing module 101, a synchronization module 102, an analysis module 103, and a control module 104. Meanwhile, although not illustrated, the scent diffusing controller 10 may further include a communication module for transmitting and receiving information and a signal with another device, a bus connecting the respective modules, and the like.

The content processing module 101 may receive the 4D contents from the content providing device 30. The 4D contents may include the AV signal and the odor effect information which interworks with the AV signal. The odor effect information may follow a standard of MPEG-V(ISO/IEC 23005). The content processing module 101 may extract the AV signal from the 4D contents and transfer the extracted AV signal to the synchronization module 102. Further, the content processing module 101 may extract the odor effect information from the 4D contents and transfer the extracted odor effect information to the analysis module 103. According to the exemplary embodiment, the 4D contents may include broadcasting contents. The odor effect information may be included in the broadcasting organization information of the broadcasting contents together with subtitles, screen description, and the like.

FIG. 3 illustrates one example of odor effect information according to an exemplary embodiment of the present invention.

Referring to FIG. 3, the odor effect information according to the exemplary embodiment of the present invention may have a format of meta data of 4D contents. The odor effect information illustrated FIG. 4 is an exemplary embodiment standardized by the MPEG-V(ISO/IEC 23005). As described above, the odor effect information according to the exemplary embodiment of the present invention may have mutual compatibility with a standardization technology according to the MPEG-V(ISO/IEC 23005).

Referring back to FIG. 2, the synchronization module 102 may generate a synchronization signal for synchronizing reproduction of the AV signal extracted from the content processing module 101 and the scent generation by the scent diffusing device 60 and transfer the generated synchronization signal to the control module 104. For example, the synchronization module 102 may decode the AV signal transferred from the content processing module 101 and periodically provide the synchronization signal to the control module 104 so that the scent diffusing device 20 diffuses the scent in synchronization with the AV signal. The synchronization module 102 may transmit the decoded AV signal to the AV device 50. According to the exemplary embodiment, the synchronization module 102 may include an AV signal reproducing function.

The analysis module 103 may receive from the content processing module 101 odor effect information received from the outside, receive the spice cartridge configuration information from the scent diffusing device 60, and receive the environment/bio information from the environment and bio sensors 41 and 42. The analysis module 103 may determine an odor to be generated by the scent diffusing device 60 based on the received information. The determined odor may be included in scent diffusing determination information to be transmitted to the control module 104.

The analysis module 103 analyzes the odor effect information received from the content processing module 101 to determine whether the scent depending on the odor effect information may be provided to the respective single spice cartridges 61 (that is, without a special combination or mixture) provided in the scent diffusing device 60. For example, the analysis module 103 may determine whether the scent depending on the odor effect information may be provided to the respective single spice cartridges 61 by comparing identities (IDs) of the spice included in the spice cartridge configuration information and the odor effect information. The spice cartridge configuration information may include information for specifying the respective spice cartridges (accurately, the spices stored in the respective spice cartridges).

For example, the information for specifying the spice cartridge includes a cartridge model number of a manufacturer. As the information for specifying the spice stored in the spice cartridge, names (e.g., a jasmine scent, a lavender scent, and the like) of scents used conventionally, a unique spice ID (alternatively, a byname thereof, for example, Chanel No. 5® by Chanel) arbitrarily defined by a spice manufacturer, or a chemical equation (e.g., methyl β-naphthyl ketone [strawberry scent, $C_{12}H_{10}O$], and the like) of a spice component may be used.

When a spice cartridge corresponding to the odor included in the odor effect information exists by referring to the spice cartridge configuration information, the analysis module 103 may make the information of the spice cartridge which exists be included in the scent diffusing determination information.

On the contrary, when the spice cartridge corresponding to the odor included in the odor effect information does not exist, the analysis module 103 may transmit to the odor server 20 the spice cartridge configuration information and the odor effect information. In respect thereto, the analysis module 103 may receive the alternate odor effect information from the odor server 20.

The alternate odor effect information may include concentration level information for combining the spices included in one or more spice cartridges among the plurality of spice cartridges 61 included in the scent diffusing device 60, and the like. For example, the alternate odor effect information may include identification information of spice cartridges to be combined, a combination ratio of the spices included in the spice cartridges, and/or information on membership grades.

The scent to be generated by the scent diffusing device 60 may be determined according to the alternate odor effect information. Information on the determined scent may be included in the scent diffusing determination information to be transmitted to the control module 104.

FIG. 4 illustrates odor effect information and spice cartridge configuration information transferred to a scent server according to an exemplary embodiment of the present invention.

Referring to FIG. 4, the odor effect information may include names of scents as many as the number corresponding to "scent_count". For example, when one of the scents to be diffused is a lilac scent, the odor effect information may include information of "scent_name=lilac". Further, the spice cartridge configuration information may include model numbers (model_number), names (cartridge_name), and vendor names (vendor_name) of the respective spice cartridges 61 mounted on the scent diffusing device 60.

FIG. 5 illustrates alternate odor effect information according to an exemplary embodiment of the present invention.

As illustrated in FIG. 5, the alternate odor effect information (mapping table) may be transferred to the analysis module 103 of the scent diffusing controller 10 from the odor server 20. The odor server 20 may generate the alternative odor effect information based on an alternate scent database 202 so as to provide an odor suitable for the user only with the spice cartridge 61 in the scent diffusing device 60 and transfer the generated odor effect information to the scent diffusing controller 10. The alternate odor effect information may include names (scent_name) of alternate scents as many as the number (scent_count) of alternate scents, a name (cartridge_name) of a spice cartridge used for diffusing the alternate scent, a scent diffusing time (operation_time), a scent diffusing intensity (scent_intensity), and a scent diffusing speed (blower_speed).

Meanwhile, the analysis module 103 receives the environment information and/or the bio information from the environment sensor 41 and/or the biosensor 42 to finally determine a scent to be diffused. The environment information may include the temperature, the humidity, the direction/strength of the wind, the position of the scent diffusing device, a distance between the scent diffusing device and the user, and the like as described above. The emotional states of the user may be derived from the bio information (e.g., a heartbeat rate, a body temperature, and the like). The scent to be diffused is determined according to the environment information and the bio information to contribute to exciting or stabilizing a psychological state of the user.

The control module 104 as a module for controlling the scent diffusing device 60 may generate the scent diffusing control message based on the scent diffusing determination information transferred from the analysis module 103. In other words, the control module 104 may generate the scent diffusing control message corresponding to the scent determined by the analysis module 103 and transmit the generated scent diffusing control message to the scent diffusing device 60. The scent diffusing control message may be information for controlling all operations associated with scent diffusing of the scent diffusing device 60 (the information is described below in detail in FIG. 6).

The control module 104 may transmit the scent diffusing control message to the scent diffusing device 60 according to the synchronization signal periodically received from the synchronization module 102. As a result, the control module 104 may synchronize the reproduction of the audiovisual contents based on the AV signal of the 4D contents and scent generation by the scent diffusing device 60.

FIG. 6 illustrates a scent diffusing control message according to an exemplary embodiment of the present invention.

The scent diffusing control message according to the exemplary embodiment of the present invention may include position information of the scent diffusing device 60, concentration information of the scent depending on the distance from the user, speed information, and direction information. Further, the scent diffusing control message may add information for simultaneously diffusing multiple scents and motion control information of the scent diffusing device by referring to the sensory effect description (SED) of MPEG-V. Since MPEG-V based odor effect information received from the content providing device 30 is standardized by considering only a most basic consumption environment, it is preferable to consider the position of the scent diffusing device, the distance, a viewer's motion, and the like together in an audiovisual environment of an actual user.

Referring to FIG. 6, start of text (STX) and end of text (ETX) may have fixed values. The STX and the ETX may indicate a start and an end of the scent diffusing control message, respectively.

Device ID represents, when several scent diffusing devices 60 are connected to the scent diffusing controller 10, an identity for distinguishing and controlling the multiple scent diffusing devices 60. For example, the Device ID may be configured as an IP address, a MAC address, a serial number, and the like.

Command Type represents a value for distinguishing a type of scent diffusing control message. For example, the Command Type may include a cleaning command, a scent diffusing command, a stand-by command, and the like.

Scent Count represents a value for indicating how many scents are diffused simultaneously.

Scent ID represents an identity for distinguishing and recognizing the spice cartridge in the scent diffusing device 60.

Operation time represents a value for determining how many seconds to diffuse the scent of the spice cartridge selected by the Scent ID for.

Scent Intensity represents a value for determining the scent diffusing concentration of the spice cartridge selected by the Scent ID.

Blower Speed represents a value for controlling the speed of the scent diffusing device 60 so as to diffuse the scent in synchronization with the AV signal according to the distance between the user and the scent diffusing device 60.

Tracking Flag represents a value for automatically tracking a spice emission direction according to a face position of the user recognized through a face recognizing device provided separately.

Swing Flag represents a value for horizontally rotating the spice emission direction so that several persons simultaneously feel the scent when the several persons simultaneously receive the 4D contents.

Figure 7:
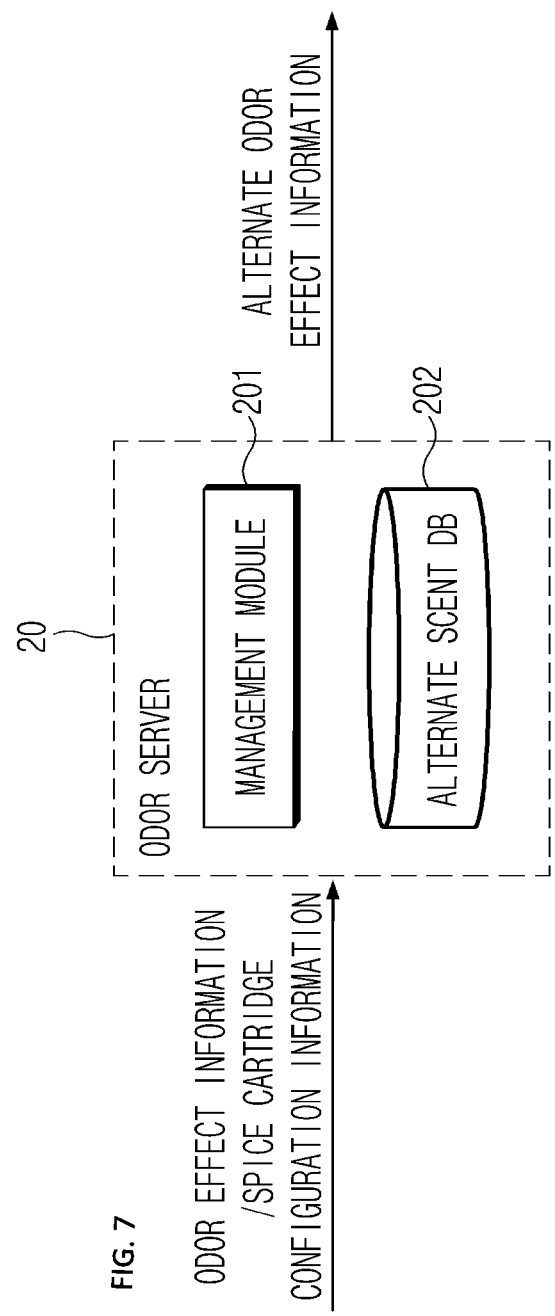
FIG. 7 illustrates an odor server according to an exemplary embodiment of the present invention.

FIG. 7 illustrates an odor server according to an exemplary embodiment of the present invention.

Referring to FIG. 7, the odor server 20 that provides the alternate odor effect information to the scent diffusing controller 10 may include a management module 201 and an alternate scent DB 202.

The management module 201 may receive the odor effect information and the spice cartridge configuration information from the analysis module 103 of the scent diffusing controller 10. The management module 201 may generate the alternate odor effect information based on the odor effect information and the spice cartridge configuration information by referring to the alternate scent DB 202. That is, when a scent (e.g., a composite scent) is included, which may not be provided to each spice cartridge 61 one to one among the scents depending on the odor effect information, the management module 201 may generate the alternate odor effect information including combination information of the spice cartridges 61. The management module 201 may return the alternate odor effect information to (the analysis module 103) of the scent diffusing controller 10.

In other words, the management module 201 may configure the alternate scent (composite scent) to be provided to the user to have a combination of the respective spices (reference scent) depending on the spice cartridge configuration information by substituting a specific scent included in the odor effect information. The composite scent as the alternate scent may not be a scent which is completely the same as the scent depending on the odor effect information (of course, both scents may be the same as each other) and the composite scent may be a scent approximate thereto. In this case, the reference scent may be a scent by the spice included in each of one or more cartridges among the plurality of spice cartridges 61.

For example, it may be assumed that the scent included in the odor effect information is scent A and the scents included in the spice cartridge configuration information are scents B, C, D, and E. In this case, the management module 201 may determine that scent A' similar to scent A may be configured by a combination of concentration levels of scents C, D, and E by referring to the alternate scent DB 202. As a result, the management module 201 may generate information on composite scent A' with which scent A is to be substituted, that is, the alternate odor effect information (e.g., data of FIG. 5) from the respective concentration levels of scents C, D, and E and transmit the generated information to the scent diffusing controller 10.

The alternate scent DB 202 may store data of various composite scents corresponding to the alternate scent. The data of the composite scent may be combined information for two or more reference scents. The combined information may include the concentration level information of the reference scents, and the like. For example, the alternate scent DB 202 may store names (and serial numbers) of various composite scents, concentration levels of the reference scents constituting the composite scent, and a membership grade between centers of the composite scent and the reference scent to correspond to each other.

FIG. 11 illustrates one example of a data structure of an alternate odor DB according to an exemplary embodiment of the present invention.

Referring to FIG. 11, the alternate scent DB 202 may store the names and serial numbers of the composite scents, the numbers and concentration levels of the reference scents constituting the composite scent, and the membership grade between the centers of the composite scent and the reference scent to correspond to each other.

The names and the serial numbers of the composite scents may be information for identifying the composite scents. For example, in a second line of FIG. 11, a composite scent of which the name is 0000 and the serial number is 01 is illustrated.

The "number and the concentration level of the reference scent" may represent the concentration level of the reference scent for implementing the composite scent. For example, in the second line of FIG. 11, in order to implement the composite scent 0000 01, it can be seen that the concentration level of reference scent 0000 is 1001, the concentration level of reference scent 0001 is 0111, the concentration level of reference scent 0010 is 0110, and the concentration level of reference scent 0011 is 1010. That is, it can be seen that the concentration levels of reference scents 0000, 0001, 0010, and 0011 for implementing composite scent 0000 01 need to be 9, 7, 6, and 10, respectively.

The membership grade may represent a grade of an association between the center of the reference scent and the composite scent. The membership grade may be used as a scale indicating a similarity degree between pattern information of the composite scent recognized from an olfactory sensor array and the reference scent. For example, a Fuzzy C-means (FCM) algorithm to be described below may be used in order to calculate the membership grade. The concentration level of the reference scent constituting the composite scent may be derived from the membership grade. However, since an error may occur in calculating the concentration level based on the membership grade due to the temperature, the humidity, deformation of a scent material according to the time, and the like, the derived concentration level of the reference scent may be updated or adjusted through a separate actual experiment.

Figure 8:
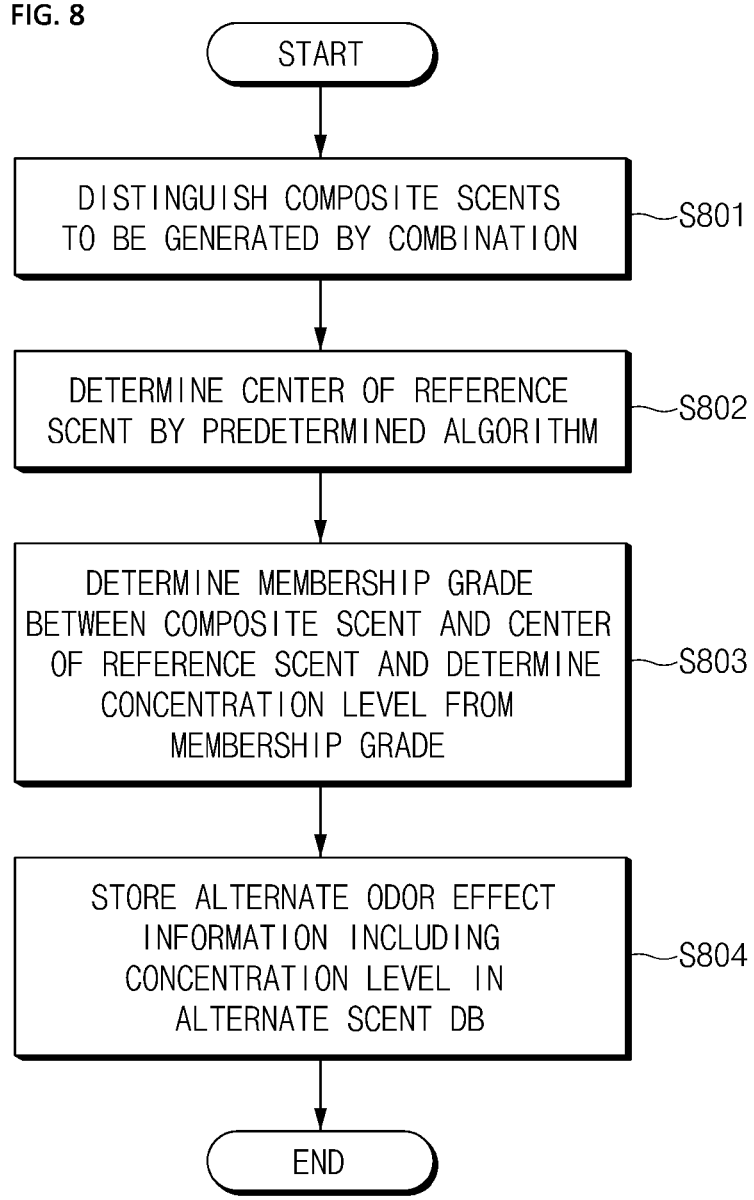
FIG. 8 is a block diagram for configuring an alternate odor DB according to an exemplary embodiment of the present invention.

FIG. 8 is a block diagram illustrating a method for configuring an alternate scent DB according to an exemplary embodiment of the present invention.

Referring to FIG. 8, in operation S801, the management module 201 may distinguish an odor which may be generated without the combination of the respective spices depending on the spice cartridge configuration information among the odors included in the odor effect information and a composite scent which needs to be generated by combining the respective spices depending on the spice cartridge configuration information. Information on the composite scent which needs to be generated by combining the respective spices depending on the spice cartridge configuration information may be constructed and stored in the alternate scent DB 202.

In operation S802, the management module 201 may set the respective odors depending on the spice cartridge configuration information as the reference scents and determine the center of each reference scent through a predetermined algorithm. According to the exemplary embodiment, the predetermined algorithm may be the Fuzzy C-means (FCM) algorithm.

In operation S803, the management module 201 may determine the membership degree between the composite scent and the center of each reference scent through the FCM algorithm. The management module 10 may derive and determine the concentration level of the reference scent constituting the actual composite scent based on the membership degree.

In operation S804, when the concentration level is determined according to a membership degree of the composite scent to the reference scent and the membership degree, the management module 201 may store information determined in association with the composite scent in the alternate scent DB 202 as the alternate odor effect information.

Figure 9:
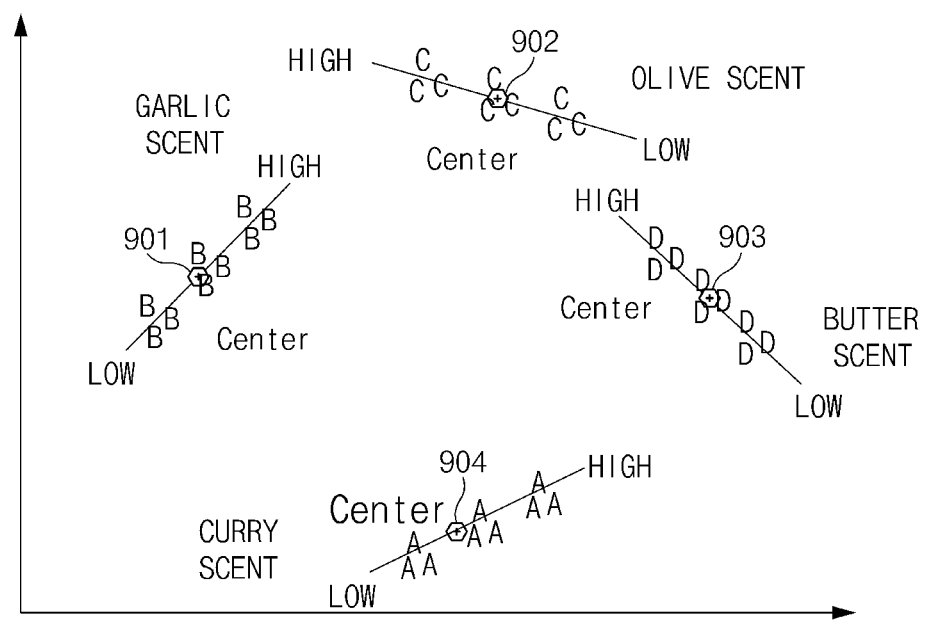
FIG. 9 illustrates a center by an FCM algorithm of a single scent according to an exemplary embodiment of the present invention.

FIG. 9 illustrates a center by an FCM algorithm of a reference scent according to an exemplary embodiment of the present invention.

Referring to FIG. 9, for example, the reference scent constituting the composite scent associated with an odor of food may include a garlic scent, an olive scent, a butter scent, and a curry scent. The various reference scents may be odors depending on the spice cartridge configuration information. That is, the garlic scent, the olive scent, the butter scent, and the curry scent may be odors by the respective separate spice cartridges 61. The respective reference scents are caused by the same odor material, but as illustrated in FIG. 9, the respective reference scents may show a predetermined pattern distribution according to a level of the concentration.

The management module 201 may determine respective centers 901, 902, 903, and 904 by applying the FCM algorithm to the reference scents. In FIG. 9, the reference scent for the odor of the food has been described, but is not limited thereto.

Figure 10A:
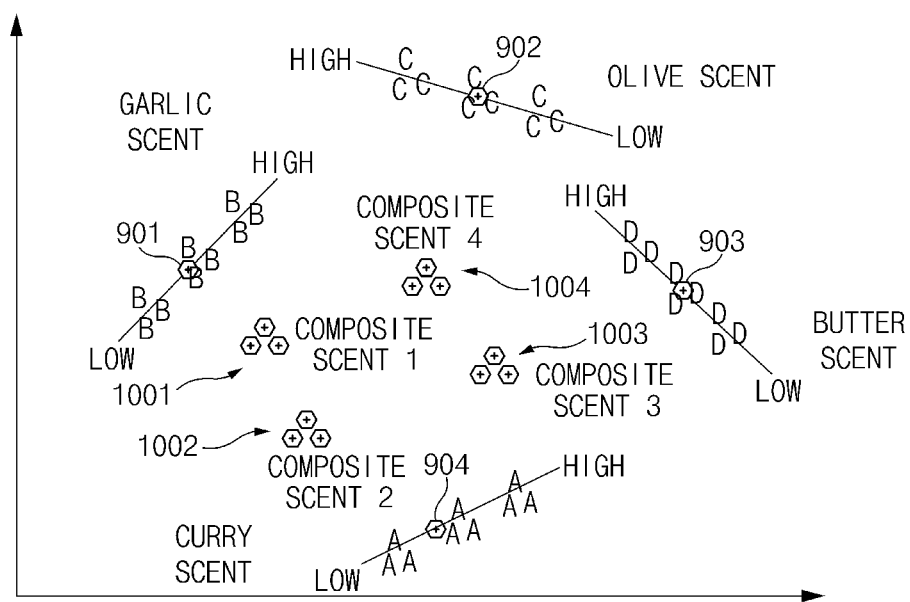
FIGS. 10A and 10B are diagrams for describing a membership grade of a composite scent to a reference scent according to an exemplary embodiment of the present invention.
Figure 10B:
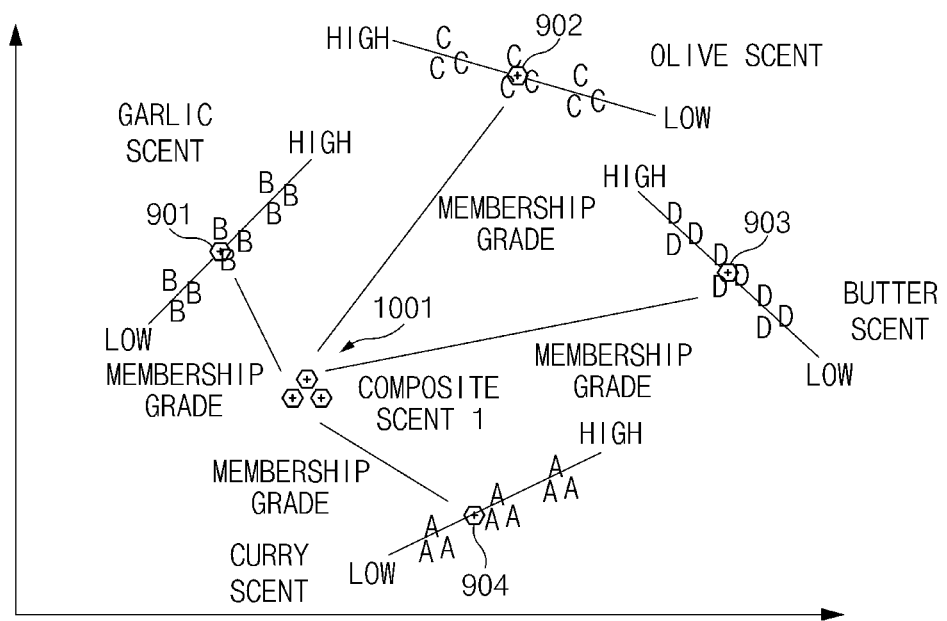

FIGS. 10A and 10B are diagrams for describing a membership grade of a composite scent to a reference scent according to an exemplary embodiment of the present invention.

Referring to FIG. 10A, for example, among the odors included in the odor effect information, the composite scents to be generated by combining the respective spices depending on the spice cartridge configuration information may be composite scents 1 to 4 1001 to 1004. Membership degrees of composite scents 1 to 4 1001 to 1004 may be determined in relationships with the reference scents through the FCM algorithm. In respect to composite scent 1 1001 among composite scents 1 to 4 1001 to 1004, as illustrated in FIG. 10B, distances between composite scent 1 1001 and the centers 901 to 904 of the respective reference scents may mean the membership grades. That is, composite scent 1 may be close to the garlic scent and the curry scent (that is, the membership grade may be high) and distant from the olive scent and the buffer scent (the membership grade may be low). The concentration levels of the reference scents for implementing the composite scent may be determined from the membership grade obtained therethrough.

FIG. 12 is a flowchart illustrating an operation of a controller 10 for a scent diffusing device according to an exemplary embodiment of the present invention.

Referring to FIG. 12, in step S1201, the controller 10 for the scent diffusing device may receive 4D contents from a content providing device 30 (e.g., a broadcasting station). The 4D contents may include an AV signal and odor effect information.

In step S1202, the controller 10 for the scent diffusing device may extract the odor effect information and the AV signal from the 4D contents.

In step S1203, the controller 10 for the scent diffusing device may receive spice cartridge configuration information from a scent diffusing device 60.

In step S1204, the controller 10 for the scent diffusing device may determine whether the spice cartridge 61 corresponding to the odor effect information extracted in step S1202 exists in the scent diffusing device 60. When the spice cartridge corresponding to the odor effect information exists in the scent diffusing device 60, the process may proceed to step S1207 and if not, the process may proceed to step S1205.

Since step S1205 is a case in which the spice cartridge corresponding to odor effect information does not exist in the scent diffusing device 60, the controller 10 for the scent diffusing device may transmit the spice cartridge configuration information and the odor effect information to an odor server 20.

In step S1206, the controller 10 for the scent diffusing device may receive alternate odor effect information from the odor server 20.

In step S1207, the controller 10 for the scent diffusing device may generate scent diffusing determination information based on the extracted odor effect information and/or the received alternate odor effect information.

In step S1208, the controller 10 for the scent diffusing device may generate a scent diffusing control message based on the scent diffusing determination information.

In step S1209, the controller 10 for the scent diffusing device may synchronize the AV signal of the 4D contents and the scent diffusing control message and transmit the AV signal and the scent diffusing control message to an AV device 50 and the scent diffusing device 60, respectively.

FIG. 13 is a flowchart illustrating an operation of an odor server according to an exemplary embodiment of the present invention.

Referring to FIG. 13, in step S1301, a management module 201 of the odor server 20 may determine the center of each reference scent by using an FCM algorithm.

In step S1302, the management module 201 may determine a membership degree between each composite scent and the center of each reference scent through the FCM algorithm.

In step S1303, the management module 201 may generate the alternate odor effect information by calculating a concentration level of each reference scent based on the membership degree between the composite scent and the center of the reference scent and store the generated alternate odor effect information in the alternate scent DB 202. In this step, the concentration level based on the membership degree is compared with a concentration level obtained through an actual experiment and when an error between both concentration levels is large, the concentration level obtained through the experiment instead of the concentration level based on the membership degree may be stored in the alternate scent DB 202.

In step S1304, the management module 201 may determine whether the odor effect information and the spice cartridge configuration information are received from the controller 10 for the scent diffusing device. When the odor effect information and the spice cartridge configuration information are not received, step S1304 may be repeated.

In step S1305, the management module 201 may generate the alternate odor effect information from the odor effect information and the spice cartridge configuration information received from the controller 10 for the scent diffusing device by referring to the alternate scent DB.

In step S1306, the management module 201 may transmit the alternate odor effect information to the controller 10 for the scent diffusing device.

According to various exemplary embodiments of the present invention, the controller for a scent diffusing device can provide an appropriate alternate odor to a user even though only a limited spice cartridge is provided. In particular, when a 4D content originator produces 4D contents only with an odor (that is, a single scent) which can be most based or representative, the user can receive an appropriate odor through a controller for a scent diffusing device according to various exemplary embodiments of the present invention. As a result, the user can sufficiently receive an emotion which is felt from the contents.

The aforementioned method of the present invention can be prepared even by a computer program. In addition, codes and code segments constituting the program can be easily deduced by a computer programmer in the art. Further, the prepared program is stored in a computer readable recording medium (information storage medium) and is read and executed by a computer to implement the method of the present invention. In addition, the recording medium includes all types of computer readable recording media.

Descriptions in the present specification as exemplary embodiments do not limit the scope of the present invention by any method. For simplification of the specification, circuit components, control systems, software, and other functional aspects of the systems in the related art may not be described. Further, connections of lines or connection members among components illustrated in the drawings exemplarily show functional connections and/or physical or circuitry connections and may be expressed as replaceable or additional various function connections, physical connection, or circuit connections in actual devices. In addition, if not mentioned in detail such as "requisite", "importantly", and the like, the component may not be a component particularly required for applying the present invention.

In the specification (in particular, claims) of the present invention, the term "the' and indication terms similar thereto may be used in both the singular number and the plural number. Further, when "range" is disclosed in the present invention, the range includes the present invention to which individual values included in the range are applied (if there is no disclosure contrary thereto) and it is the same as the respective individual values constituting the range being disclosed in the detailed description of the present invention. All examples or exemplary terms (e.g., etc.) in the present invention are just used for, in detail, describing the present invention and if the examples or exemplary terms are not limited by the claims, the range of the present invention is not limited by the examples or exemplary terms. Further, it can be appreciated by those skilled in the art that various modifications, combinations, and changes may be configured according to a design condition and a design factor within a scope of the appended claims or the equivalent thereto.

The present invention described as above is not limited by the aforementioned exemplary embodiments and the accompanying drawings because it will be apparent to those skilled in the art that various substitutions, modifications, and changes can be made within the scope without departing from the technical spirit of the present invention.

What is claimed is:

1. A controller for a scent diffusing device for controlling a scent diffusing device including a plurality of spice cartridges, the controller comprising:
   an analysis module determining an odor to be generated by the scent diffusing device based on odor effect information and configuration information of the plurality of spice cartridges, wherein the configuration information includes information for specifying reference scents of spices included in respective spice cartridges; and
   a control module transmitting a scent diffusing control message corresponding to the determined odor to the scent diffusing device so that the scent diffusing device diffuses the determined odor,
   wherein when a spice cartridge corresponding to the odor effect information does not exist among the plurality of spice cartridges, the analysis module transmits to a server the configuration information of the plurality of spice cartridges and the odor effect information, receives from the server alternate odor effect information generated based on the odor effect information and a similarity between a composite scent and the reference scents, and determines the odor to be generated by the scent diffusing device according to the alternate odor effect information.

2. The controller of claim 1, wherein the alternate odor effect information includes concentration level information for combining the spices included in the respective spice cartridges.

3. The controller of claim 1, further comprising:
   a content processing module receiving contents including an AV signal and odor effect information which interlocks with the AV signal extracting the AV signal from the contents; and
   a synchronization module generating a synchronization signal for synchronizing reproduction of the extracted AV signal and odor generation by the scent diffusing device and transferring the generated synchronization signal to the control module,
   wherein the control module transmits the scent diffusing control message to the scent diffusing device according to the synchronization signal.

4. The controller of claim 3, wherein the contents includes broadcasting contents, and
   the odor effect information is included in broadcasting organization information for the broadcasting contents.

5. The controller of claim 1, wherein at least one of the odor effect information and the scent diffusing control message follows an MPEG-V standard.

6. A server for providing alternate odor effect information to a controller of a scent diffusing device, which controls a scent diffusing device, the server comprising:
   a management module receiving odor effect information and configuration information of a plurality of spice cartridges included in the scent diffusing device from the controller, wherein the configuration information includes information for specifying reference scents of spices stored in respective spice cartridges, and wherein the management module generates, when a spice cartridge corresponding to the odor effect information does not exist among the plurality of spice cartridges, the alternate odor effect information based on the odor effect information and a similarity between a composite scent and the reference scents; and
   an alternate scent database for storing the alternate odor effect information,
   wherein the reference scents are odors by spices included in respective spice cartridges, and
   wherein the management module returns the alternate odor effect information to the controller which controls the scent diffusing device to diffuse an odor according to the alternate odor effect information.

7. The server of claim 6, wherein the alternate odor effect information includes concentration level information of the reference scents.

8. The server of claim 7, wherein the concentration level information is based on a membership grade representing an association between the composite scent and centers of respective reference scents.

9. The server of claim 8, wherein the membership grade is obtained by using a Fuzzy C-means (FCM) algorithm.

* * * * *